US011408854B2

(12) United States Patent
Baig et al.

(10) Patent No.: US 11,408,854 B2
(45) Date of Patent: Aug. 9, 2022

(54) MAGNETO-OPTICAL DETECTION AND DISCERNMENT OF BIOFLUID CRYSTALS

(71) Applicant: CASE WESTERN RESERVE UNIVERISTY, Cleveland, OH (US)

(72) Inventors: Tanvir Baig, Cleveland, OH (US);
Robert Brown, Solon, OH (US);
Robert Deissler, Fairview Park, OH (US); Brian T. Grimberg, Cleveland Heights, OH (US); Abdullah Amin, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 850 days.

(21) Appl. No.: 15/686,811

(22) Filed: Aug. 25, 2017

(65) Prior Publication Data

US 2019/0064113 A1    Feb. 28, 2019

(51) Int. Cl.
*G01N 27/74* (2006.01)
*G01N 33/487* (2006.01)
*G01R 33/032* (2006.01)

(52) U.S. Cl.
CPC ........... *G01N 27/74* (2013.01); *G01N 33/487* (2013.01); *G01R 33/032* (2013.01)

(58) Field of Classification Search
CPC ..... G01N 27/74; G01N 33/487; G01R 33/032
See application file for complete search history.

(56) References Cited

U.S. PATENT DOCUMENTS

| 5,978,694 | A | 11/1999 | Rapoport | |
|---|---|---|---|---|
| 8,214,006 | B2 | 7/2012 | Newman et al. | |
| 8,481,282 | B2 | 7/2013 | Levine et al. | |
| 8,586,389 | B2 * | 11/2013 | Woolverton | G01N 33/5438 436/526 |
| 9,575,052 | B2 | 2/2017 | Grimberg et al. | |
| 9,778,245 | B2 | 10/2017 | Grimberg et al. | |
| 2006/0025659 | A1 | 2/2006 | Kiguchi et al. | |
| 2006/0126990 | A1 * | 6/2006 | Deng | G01R 33/032 385/12 |
| 2010/0149519 | A1 | 6/2010 | Toofan | |
| 2015/0125873 | A1 | 5/2015 | Newman et al. | |
| 2015/0377857 | A1 * | 12/2015 | Grimberg | G01N 1/28 356/39 |
| 2020/0085340 | A1 * | 3/2020 | Baig | A61B 5/05 |
| 2021/0109094 | A1 * | 4/2021 | Deissler | B01L 3/502761 |
| 2021/0389315 | A1 * | 12/2021 | Brady-Kalnay | C12Q 1/6888 |

* cited by examiner

*Primary Examiner* — Lore R Jarrett
(74) *Attorney, Agent, or Firm* — Tarolli, Sundheim, Covell & Tummino LLP

(57) ABSTRACT

A diagnostic device is described herein that can be used to perform magneto-optical detection and discernment of crystals within a biofluid sample. A magnetic field can be applied by the diagnostic device in a direction relative to light traveling through the sample. The presence of a crystal can be determined based on the magneto-optical properties of the sample. The detected crystal can be one of two similar crystal types that may be in the biofluid sample. The two similar crystal types can exhibit different magneto-optical properties under a magnetic field in a different direction. Accordingly, the type of crystal can be discerned by applying the magnetic field in the different direction as light travels through the sample. Discernment of the type of crystal can lead to diagnosis of the particular disease condition and subsequent proper treatment of the disease condition.

8 Claims, 15 Drawing Sheets

MAGNETO-OPTICAL DETECTION AND DISCERNMENT OF BIOFLUID CRYSTALS

TECHNICAL FIELD

This disclosure relates generally to detection and discernment of biofluid crystals and, more specifically, to magneto-optical detection of crystals in a biofluid sample and diagnosis of a disease condition based on a discernment of the detected crystals.

BACKGROUND

Generally, a biofluid can be any type of fluid originating from inside the body of a living organism, such as: urine, sweat, breast milk, synovial fluid, blood, cerebrospinal fluid, blister fluid, cyst fluid and the like. Certain disease conditions can be caused by the accumulation of crystals within a biofluid. Therefore, detection of the crystals in the biofluid is an important first step in diagnosis of a disease condition. However, similar disease conditions related to accumulation of crystals in a biofluid (like gout and pseudogout) may have different crystals, which require different treatments. Discerning the type of crystal is important to ensure that the disease condition is treated properly.

Traditionally the gold standard for detection and diagnosis of disease conditions related to accumulation of crystals has been polarized light microscopic analysis of the affected biofluid. Polarized light microscopy can detect the existence of crystals and composition of the crystals can be further analyzed and classified based on compensated birefringence (two refractive indices arise due to crystal anisotropy) patterns. The process of polarized light microscopy requires trained clinicians or other personnel with adequate laboratory facilities, which are often lacking in the primary-care setting, where most patients are diagnosed. As a result, these patients are diagnosed with the disease based on clinical symptoms. For example, the diagnosis of gout can be based on clinical symptoms defined by the American Rheumatology Association (ARA), but these diagnoses are wrong about 30% of the time; pseudogout does not have any well-established guidelines for diagnosis. Other approaches such as radiographs and serum analysis, suffer from low sensitivity and/or low specificity. Electron microscopy, atomic force microscopy and X-ray diffraction can provide more accurate information about crystals but these methods are technically demanding, expensive and not available in most clinical facilities.

SUMMARY

The present disclosure relates to diagnostic devices, systems, and methods that can be used to perform magneto-optical detection and discernment of crystals within a biofluid sample. The presence of crystals can be first detected in the biofluid sample by applying a magnetic field in a direction as light travels through the sample. The detected crystal can be one of two similar crystal types that may be in the biofluid sample. The two similar crystal types can exhibit different magneto-optical properties under a magnetic field in a different direction. Accordingly, the type of crystal can be discerned by applying the magnetic field in the different direction as light travels through the sample. Discernment of the type of crystal can lead to diagnosis of the particular disease condition and subsequent proper treatment of the disease condition.

In accordance with an aspect of this disclosure, a device is provided that can detect crystals in a biofluid sample and discern the type of crystals. The diagnostic device includes a light source to transmit a light beam through the biofluid sample to a light detector. The diagnostic device also includes a plurality of magnets. The sample and/or at least one of the plurality of magnets is movable to a first magnetic field position in a first magnet configuration to a second magnetic field position in a second magnet configuration. A first magnetic field is directed through the sample at a first direction in the first magnetic field position and a second magnetic field is directed through the sample at a second direction in the second magnetic field position. The device also includes a sampling device that samples the light detector with the sample at the first magnetic field position to determine an existence of a concentration of crystals in the biofluid sample and with the sample at the second magnetic field position to distinguish a type of crystals in the biofluid sample.

In accordance with another aspect of this disclosure, a method is provided for detecting crystals in a biofluid sample and discerning the type of crystals. The method can include transmitting a light beam through a biofluid sample to a light detector. The method can also include establishing a first magnetic field directed through the sample at a first direction relative to the sample; and determining whether a concentration of crystals exists in the biofluid sample based on recordings of the light beam under the first magnetic field. When the concentration of crystals is found to exist in the biofluid sample, the method can also include establishing a second magnetic field directed through the sample at a second direction relative to the sample; and identifying a type of the biofluid crystals based on recordings of the light beam under the second magnetic field.

In accordance with a further aspect of this disclosure, a system is provided for detecting crystals in a biofluid sample and discerning the type of crystals. The system includes a light source to transmit a light beam through a biofluid sample to a light detector. The system can also include a first plurality of permanent magnets and a second plurality of permanent magnets. The sample is movable from a first magnetic field position surrounded by the first plurality of permanent magnets and a second magnetic field position within the second plurality of permanent magnets in a second magnetic field position surrounded by the second plurality of magnets. A first magnetic field is directed through the sample at a first direction in the first magnetic field position and a second magnetic field is directed through the sample at a second direction in the second magnetic field position, wherein the first direction and the second direction are different directions and generally perpendicular to each other. The system also includes a sampling device that samples the light detector with the sample at the first magnetic field position to determine an existence of a concentration of crystals in the biofluid sample and with the sample at the second magnetic field position to distinguish a type of crystals in the biofluid sample.

In accordance with another aspect of this disclosure, devices, systems and methods are provided for detecting crystals in a biofluid sample and discerning the type of crystals by applying the same magnetic field, but with a different polarization direction. The presence of crystals can be first detected in the biofluid sample by applying a magnetic field in a direction as light travels through the sample. The detected crystal can be one of two similar crystal types that may be in the biofluid sample. The two similar crystal types can exhibit different magneto-optical properties under a magnetic field, but with the polarization direction of the light being in a different direction. Accordingly, the type of crystal can be discerned by changing the polarization direction of the light and then again applying the magnetic field as light travels through the sample. Discernment of the type of crystal can lead to diagnosis of the particular disease condition and subsequent proper treatment of the disease condition.

BRIEF DESCRIPTION OF THE DRAWINGS

The features, objects, and advantages of the invention will become more apparent from the detailed description set forth below when taken in conjunction with the drawings, wherein.

DETAILED DESCRIPTION OF THE INVENTION

The present disclosure relates to diagnostic devices, systems, and methods that can be used to perform magneto-optical detection and discernment of crystals within a biofluid sample. When crystals are suspected of being in the biofluid sample, light can be shined through the biofluid sample. A magnetic field at a first direction relative to the light can be applied, and a change in intensity of light passing through the sample under the magnetic field can be detected. Based on the change in light intensity detected, the presence of crystals can be determined. When it is determined that the sample contains crystals another magnetic field in a different direction can be applied to the sample. Alternatively, instead of changing the magnetic field direction, the polarization direction of the light can be changed and the same magnetic field can be applied. Depending on the light intensity detected after passing through the sample in the presence of the magnetic field in the second direction or with a different polarization direction of the light, the type of crystal can be determined. For example, the diagnostic devices, systems, and methods of this disclosure can distinguish between monosodium urate (MSU) crystals (corresponding to a diagnosis of gout) and calcium pyrophosphate dihydrate (CPPD) crystals (corresponding to a diagnosis of pseudogout) in a synovial fluid sample.

Magneto-optical detection provides an improvement over other techniques used to detect crystals in biofluids. In many cases, the detection of crystals requires specially trained operators with adequate laboratory facilities, and primary care settings tend to be devoid of one or both. In contrast, the diagnostic devices, systems, and methods described herein are automated, efficient, and low cost, allowing crystals to be detected and identified at the point of care (e.g. in an emergency room, a doctor's office or veterinarian's office). However, the diagnostic devices, systems, and methods may also be used, at least in part, in a laboratory setting.

Figure 1:
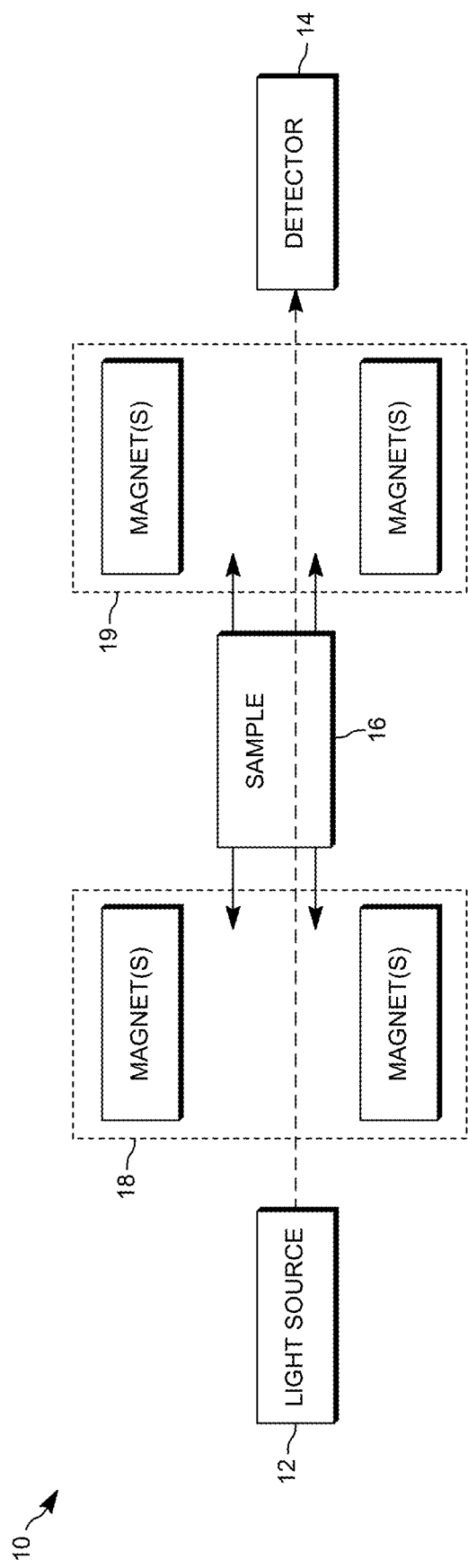
FIG. 1 is a block diagram of an example diagnostic device that can be used to detect and discern crystals in a biofluid sample based on one or more magneto-optical properties.
Figure 2:
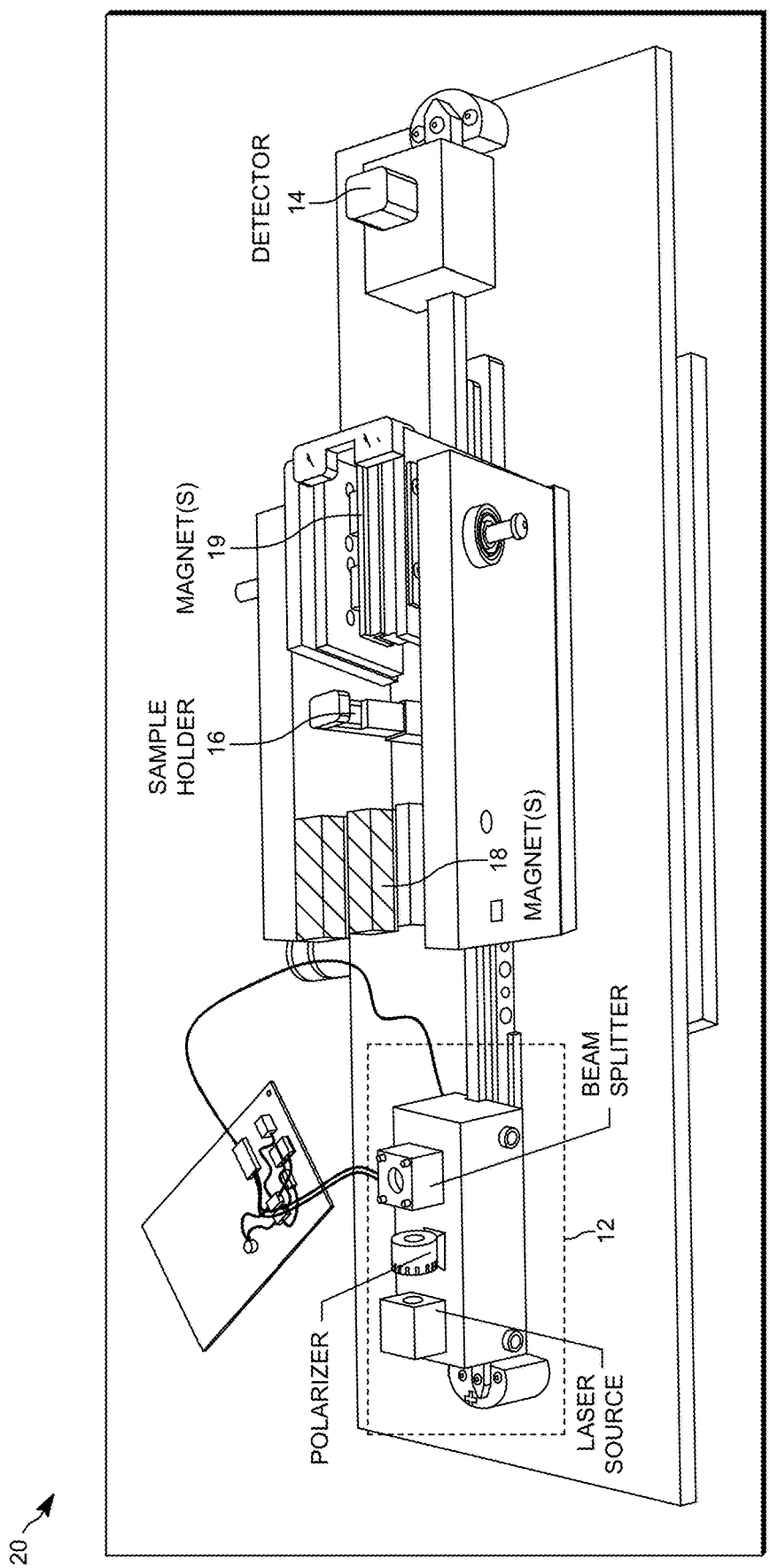
FIG. 2 is an illustration of a prototype of an example diagnostic device.

FIG. 1 shows an example diagnostic device 10 that can be used to detect and discern crystals in a sample based on one or more magneto-optical properties. An illustration of a prototype 20 of the example diagnostic device is shown in FIG. 2. It will be noted that the device 10 can also be used as part of a system that includes one or more controllers or other computing device, which can be used to operate the diagnostic device 10 in at least a partially automated fashion. For example, the controller or other computing device can interface with one or more components of the diagnostic device 10 to control delivery of light, recording of data, configuration of the diagnostic device, or the like.

The diagnostic device 10 can include a light source 12, a light detector 14, and a sample 16 in a sample holder between the light source 12 and the detector 14. The light source 12 can transmit a light beam (dashed line) through the sample 16 to the light detector 14. In the example shown in FIG. 2, the light source 12 can include a laser light source. The light from the laser light source can be polarized by a polarizer (e.g. a linear polarizer, a circular polarizer, or the like). As an example, a linear polarizer can create horizontally polarized light. The polarizer can be part of the light source 12 to provide a polarized laser source. A beam splitter can also be part of the light source 12. The beam splitter can aid in power control and/or data collection. For example, the beam splitter can provide a first portion of the light beam through the sample 16 and send a second portion to another detector (not shown). The detected second portion can be used to normalize the intensity of the light beam detected by the detector 14 after traveling through the sample 16. The detector 14 can detect the light beam that has travelled through the sample 16.

As an example, the detector 14 can include one or more photodetectors. Detection by the detector 14 can be controlled by a sampling device. The sampling device can record detections by the detector 14 according to a sampling frequency. The sampling frequency can differ based on the application. As an example, the sampling frequency can be sufficient to sample the light detector to determine transmission intensities of the light beam. The sampling device, as another example, can include a processing unit and can be used to determine the transmission intensities of the light beam. Based on the transmission intensities, the sampling device can classify a type of crystal in the biofluid sample. The sampling device can include a non-transitory memory with baseline intensity values corresponding to two or more different potential classifications of the crystal. The selected classification, or other information, can be output from the sampling device.

The sample 16 can include a biofluid. The term "biofluid" refers to any type of fluid originating from inside the body of a living organism. Biofluids can be excreted (such as urine or sweat), secreted (such as breast milk), obtained with a needle (such as synovial fluid, blood or cerebrospinal fluid), or develop as a result of a pathological process (such as blister fluid or cyst fluid). The biofluid may include a concentration of crystals, which can be indicative of a disease or condition. In some instances, the crystals within the biofluid can offer physical phenomena that are considerably different from the optical, electronic and mechanical properties exhibited by conventional solids, such as covalent or ionic crystals. In some examples, the biofluid sample may be diluted in a substance that is substantially inert (e.g. a buffer). Additionally, the biofluid may undergo a digestive process to better reveal components of the biofluid (like the crystals) in the sample 16.

As an example, the biofluid can be synovial fluid. Types of crystals that may exist in the synovial fluid include monosodium urate (MSU), which is indicative of gout, and calcium pyrophosphate dihydrate (CPPD), which is indicative of pseudogout. Other examples of biofluids can have other associated crystals. Oxalate crystals and/or struvite crystals can be found in urine as indicators of kidney stones or bladder stones, respectively.

The device 10 can include a plurality of magnets. As shown in FIG. 1, the plurality of magnets can include a first group of magnets 18 and a second group of magnets 19. However, in some instances, only the first group of magnets 18 or the second group of magnets 19 may be necessary for the device 10. Additionally, the sample and/or the plurality of magnets can be moveable to establish magnetic fields in directions relative to the light.

As shown in FIG. 1, the sample 16 can be moved from a center position to a position within the first group of magnets 18 and a position within the second group of magnets 19. The first group of magnets 18 and the second group of magnets 19 can each establish a magnetic field in one or more directions through the sample 16. For example, the first group of magnets 18 and/or the second group of magnets 19 can be moveable to different positions around the sample 16. Alternatively, the sample 16 can be positioned in a location and one or more of the plurality of magnets can be moved around the sample.

In the example of FIG. 1, the first group of magnets 18 can include two or more magnets that are moveable into different orientations to establish a magnetic field in a direction relative to the light. The second group of magnets 19 can include two or more magnets that are moveable into different orientations to establish a magnetic field in other directions relative to the light. For example, the second group of magnets 19 can include 2, 4, 6, 8, or more magnets to establish the magnetic field in the other directions relative to the light. The different arrangement of the magnets 18 and magnets 19 can affect crystals within the sample 16, and the light can be affected in different manners based on the presence of crystals within the sample.

The first group of magnets 18 and/or the second group of magnets 19 can be simple, inexpensive lab magnets. However, one or more of the first group of magnets 18 and/or the second group of magnets 19 can be a permanent magnet. Generally, permanent magnets can produce a high magnetic field with a low mass. For example, the magnetic field can be between about 0.01 T and about 100 T. As another example, the magnetic field can be between about 0.1 T and 10 T. As a further example, the magnetic field can be between 0.1 T and 2 T. Additionally, a permanent magnet is generally stable against demagnetizing influences. For example, this stability may be due to the internal structure of the magnet. The permanent magnet can be made from a material that is magnetized and creates its own persistent magnetic field. The permanent magnet can be made of a hard ferromagnetic material, such as alcino or ferrite. However, the permanent magnet can also be made of a rare earth material, such as samarium, neodymium, or respective alloys.

As another example, one or more of the first group of magnets 18 and/or the second group of magnets 19 can be an electromagnet. An electromagnet can be made from a coil of a wire that acts as a magnet when an electric current passes through it, but stops being a magnet when the current stops. The coil can be wrapped around a core of a soft ferromagnetic material, such as steel, which greatly enhances the magnetic field produced by the coil.

The device 10 can be used for detection (shown in FIGS. 3-5) and discernment (shown in FIGS. 6-8) of crystals in the biofluid sample 16. As described herein the device 10 can detect and distinguish between gout and pseudogout when the sample 16 includes synovial fluid. The device 10 can be used for detection and discernment of other types of crystals in other biofluid samples. Additionally, the device 10 can be configured to deliver a magnetic field in yet another direction (shown in FIGS. 6, 9, and 10).

Gout and pseudogout are two of the most common crystal-induced arthropathies and are each due to the accumulation of crystals in synovial fluid. Gout is caused by monosodium urate (MSU) crystals, while pseudogout is caused by calcium pyrophosphate dihydrate (CPPD) crystals. Although caused by the accumulation of different crystals in a patient's synovial fluid, both gout and pseudo gout are forms of inflammatory arthritis resulting in similar symptoms during flare ups, such as a swollen joint and excruciating pain. While gout can be treated with medications to lower the high uric acid levels causing the accumulation of MSU crystals, there is no medication to remove the CPPD crystals of pseudogout from joints. Distinguishing an acute inflammatory arthritis attack as either gout or pseudogout is necessary for proper treatment.

A patient can present with a swollen joint (like a toe) causing pain. An amount of synovial fluid can be aspirated from the joint and at least a portion of the fluid can undergo digestion and dilution to make up the biofluid sample 16. Without the magnetic field, crystals in the biofluid are randomly organized in the sample 16. When exposed to a magnetic field, the crystals can become organized in a pattern based on the direction of the magnetic field.

Figure 3:
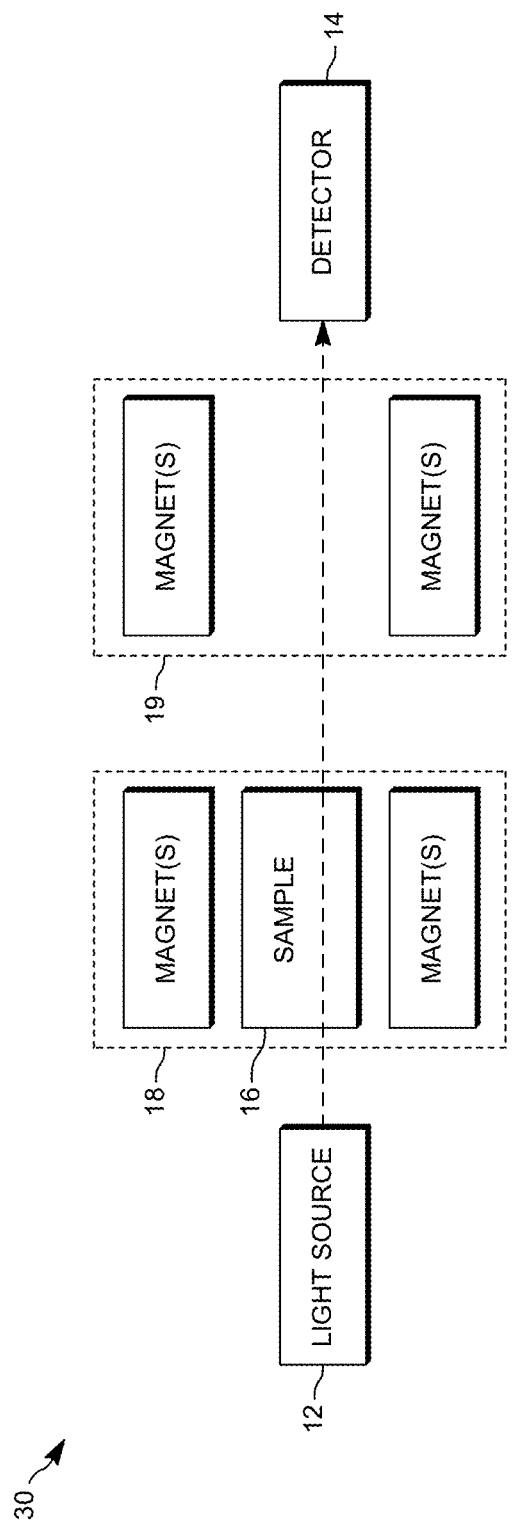
FIG. 3 is a block diagram of the example diagnostic device configured to detect crystals in a biofluid sample.
Figure 4:
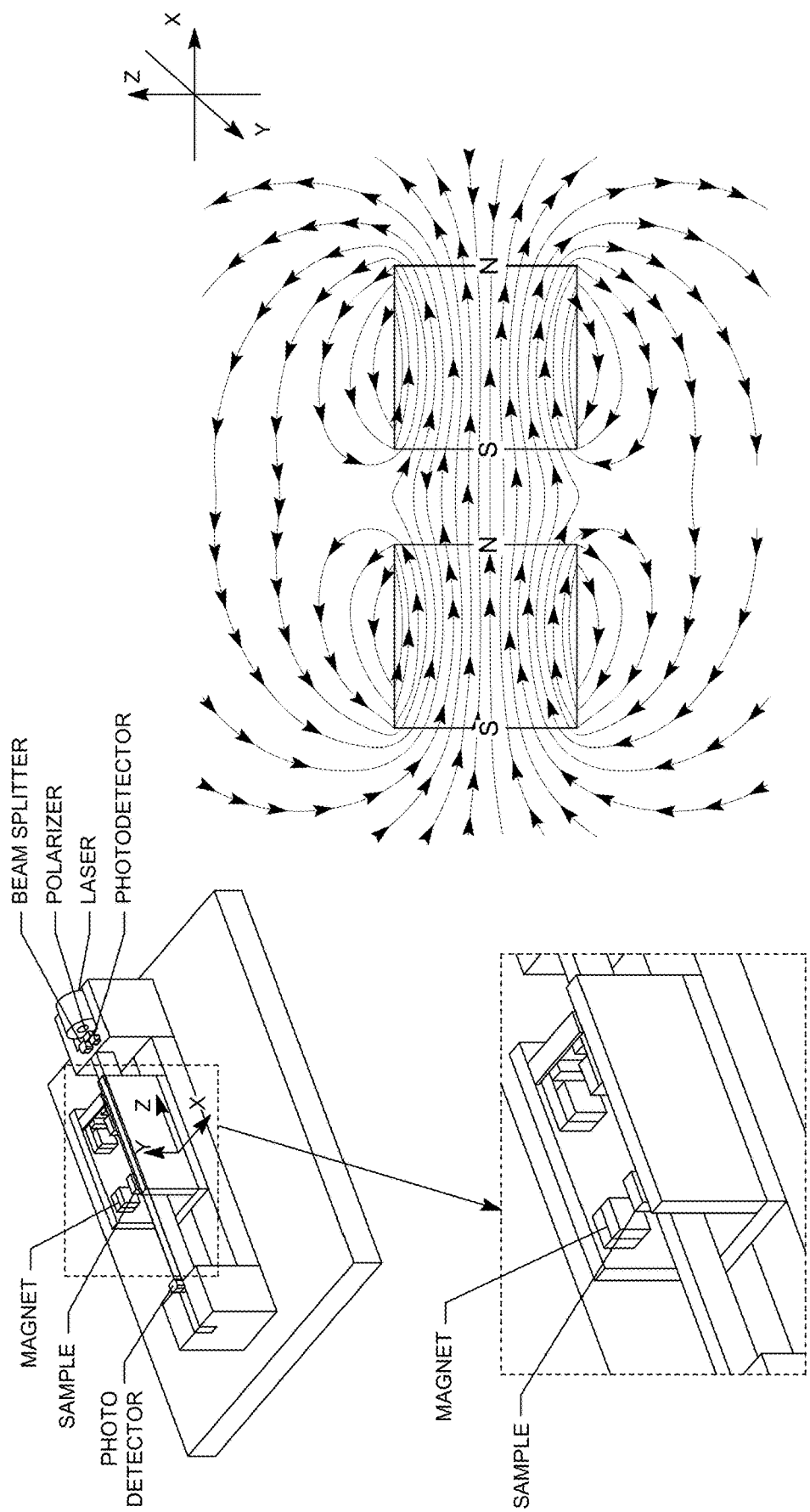
FIG. 4 is an illustration of an example of the magnetic field that can be delivered to detect crystals in the biofluid sample.

First, it can be determined whether the biofluid sample 16 includes crystals using the device configuration shown in FIG. 3. FIG. 3 shows an example 30 where the sample 16 has been moved or placed within the first group of magnets 18. The first group of magnets 18 can be arranged to deliver a magnetic field to the sample 16 in a direction relative to the sample (dashed line). One or more of the first group of magnets 18 can be configured for rotational movement or linear movement to deliver the magnetic field to the sample 16. The second group of magnets 19 can be shielded so not to deliver a magnetic field that affects the sample. As shown in FIG. 4, the magnetic field can be applied in a "horizontal" direction "perpendicular" to the light beam (the magnetic field is established in a direction along the x-axis, while the light beam travels along the y-axis). In FIG. 4, the first group of magnets 18 can be arranged so that a north (N) side of a first magnet lines up with a south (S) side of a second magnet and a magnetic field is established there between.

Figure 5:
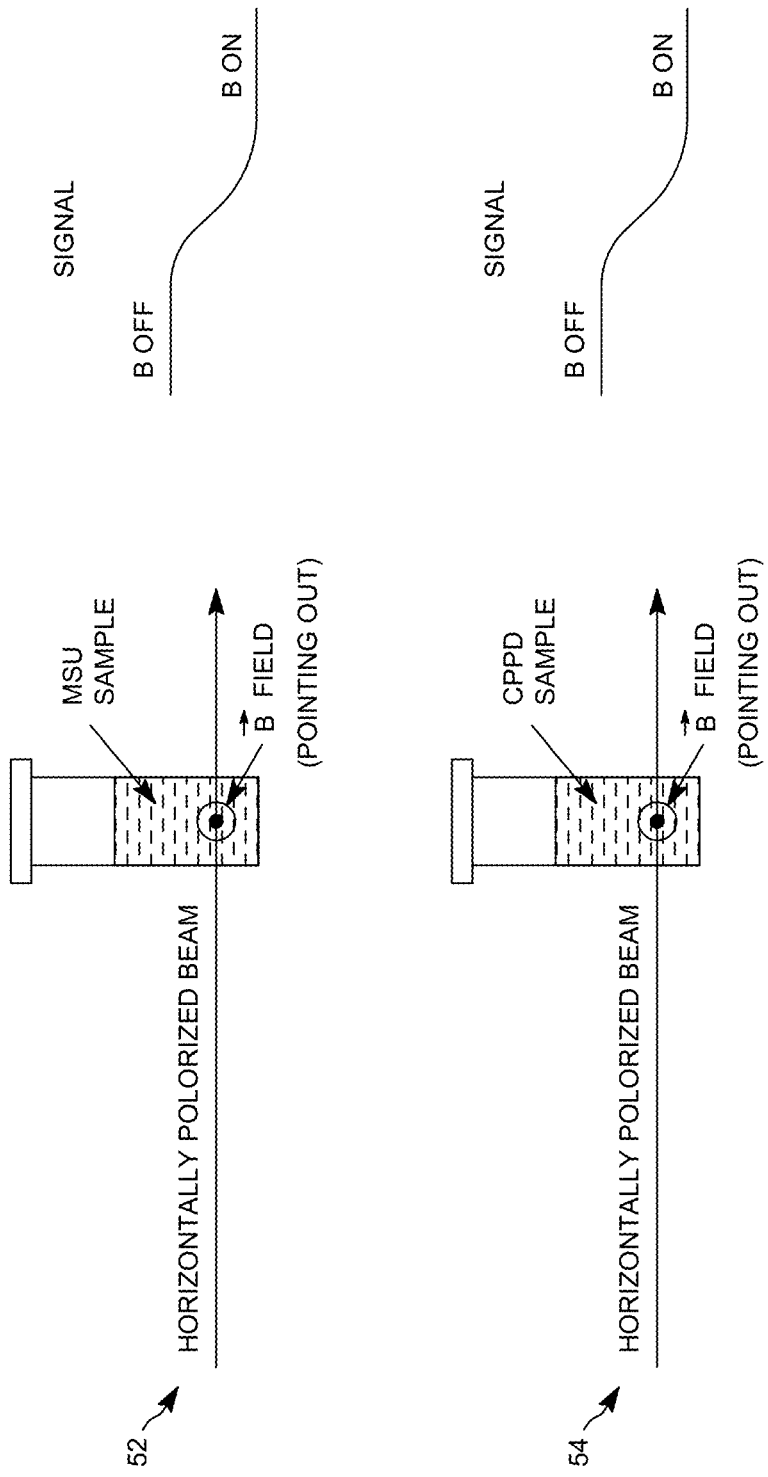
FIG. 5 is an illustration of example light signals under application of the magnetic field shown in FIGS. 3-4 used in detection of crystals in the biofluid sample.

FIG. 5 shows the resulting light signal in the presence of crystals in the fluid. Element 52 shows the effect of MSU crystals of gout, while element 54 shows the effect of CPPD crystals of pseudogout. The signals of elements 52 and 54 both exhibit a lower intensity after traversing the sample 16 with the magnetic field turned on in the horizontal perpendicular direction. When the light signal decreases in intensity with the magnetic field on in the horizontal perpendicular direction, the presence of crystals can be confirmed. However, if the light signal does not decrease in intensity with the magnetic field on in the horizontal perpendicular direction, no crystals are found and the diagnosis becomes not gout or pseudogout.

Figure 6:
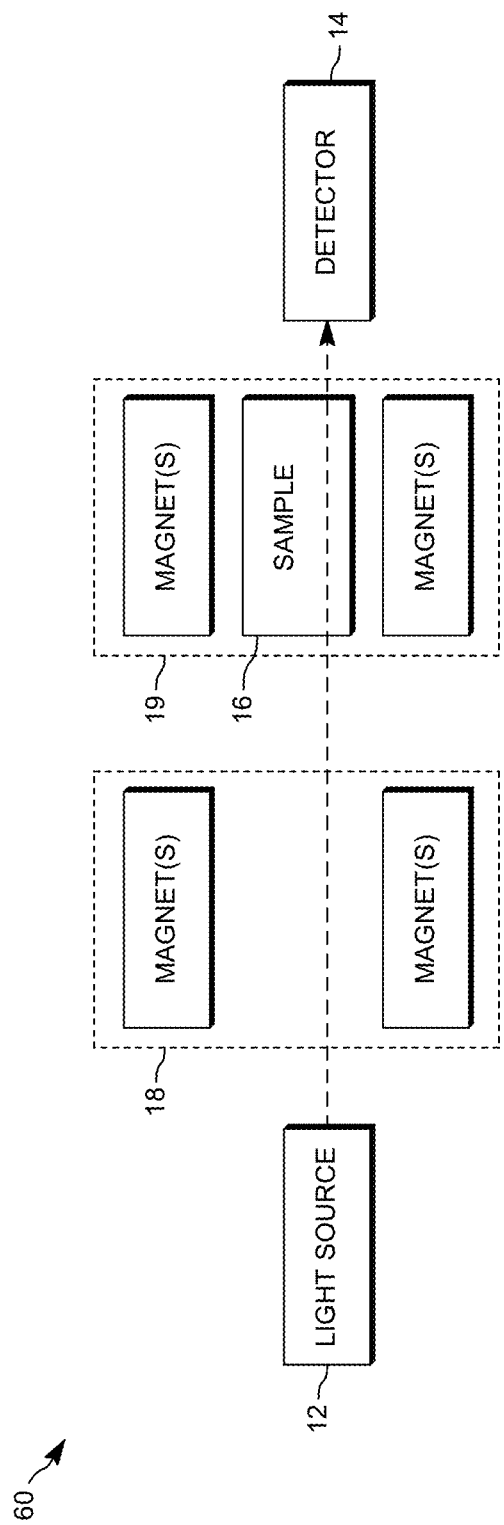
FIG. 6 is a block diagram of the example diagnostic device configured to discern crystals in a biofluid sample.

When crystals are detected in the sample 16, further discernment is performed. The sample 16 can be moved to be within the second group of magnets 19, as shown in FIG. 6. The second group of magnets 19 can be arranged to deliver a magnetic field to the sample 16 in a direction relative to the sample (dashed line). One or more of the second group of magnets 19 can be configured for rotational movement or linear movement to deliver the magnetic field to the sample 16 in a direction different than the one used for detection. The first group of magnets 18 can be shielded so as not to deliver a magnetic field that affects the sample.

Figure 7:
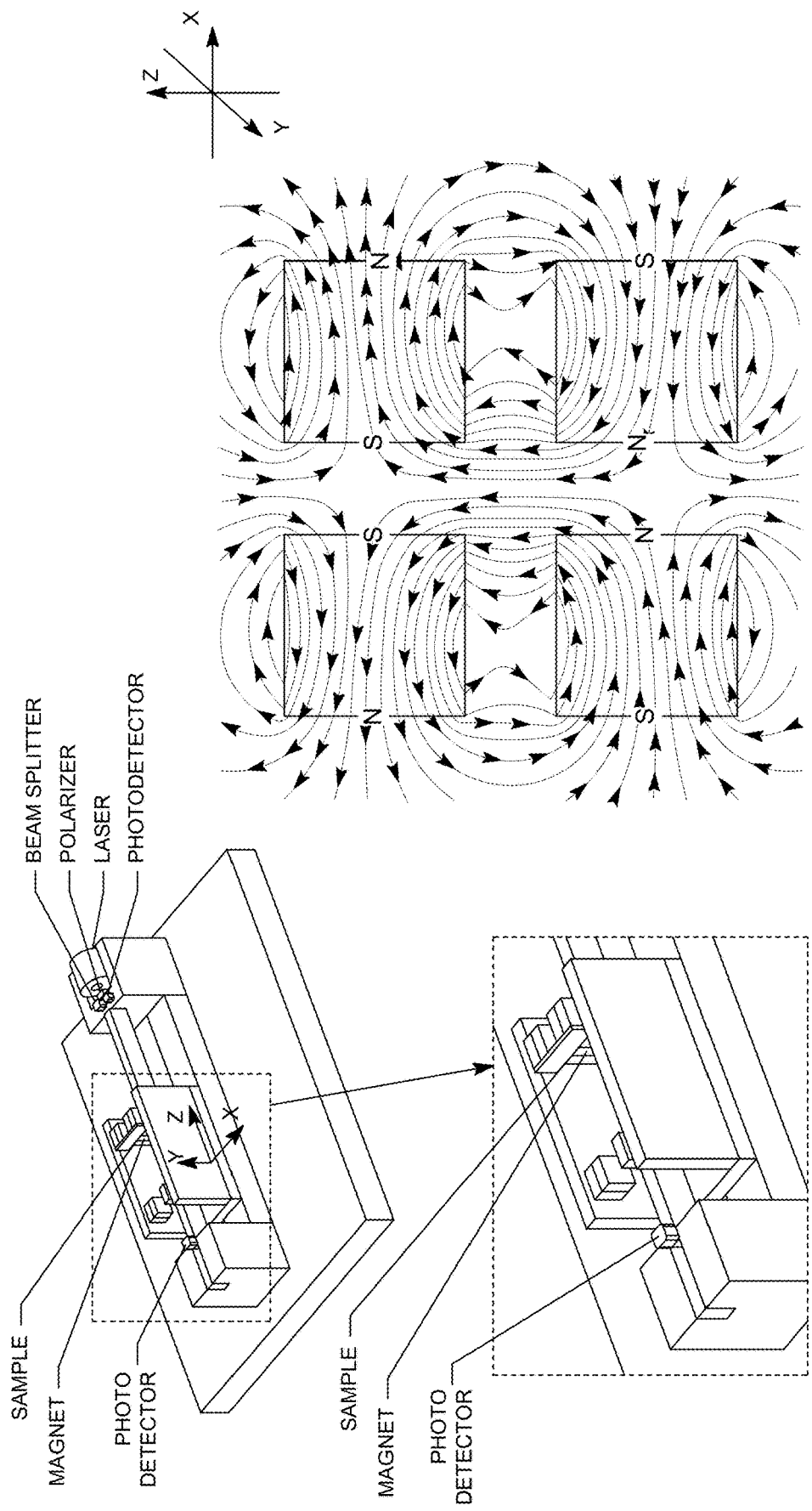
FIG. 7 is an illustration of an example of the magnetic field that can be delivered to discern crystals in the biofluid sample.

The different reactions of the crystals to the magnetic field in the different direction can be used to distinguish between types of the crystals. As shown in FIG. 7, the magnetic field can be applied in a "vertical" direction "perpendicular" to the light beam (the magnetic field is established in a direction along the y-axis, while the light beam travels along the z-axis). In some instances, the application of the magnetic field in the vertical perpendicular direction may be the only direction of the magnetic field that is necessary to fully distinguish between MSU and CPPD crystals.

Figure 8:
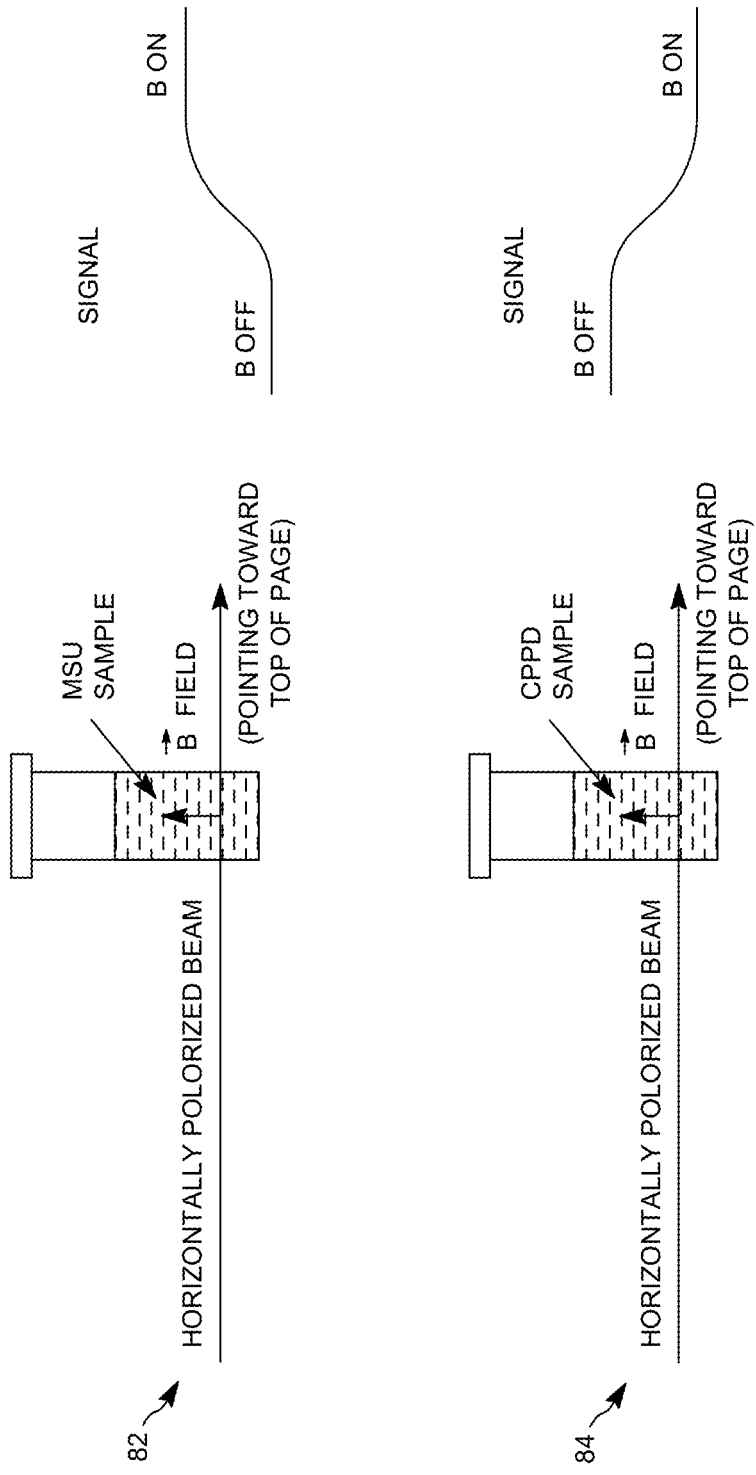
FIG. 8 is an illustration of example light signals under application of the magnetic field shown in FIGS. 6-7 used in discernment of crystals in the biofluid sample.

Four magnets of the second group of magnets 19 are shown in FIG. 7, with south sides (S) of the top two magnets aligned horizontally and north sides (N) of the bottom two magnets aligned horizontally. The different crystals have different effects on the intensity of light that traveled through the sample under the vertical magnetic field. As shown in FIG. 8, the light signal increases with MSU and decreases with CPPD. This phenomenon can be due to differences in the dichroic nature of MSU and CPPD. Accordingly, the crystals can be identified as MSU or CPPD crystals by this distinguishing response. The identified crystal can be used to diagnose gout or pseudogout, respectively.

Figure 9:
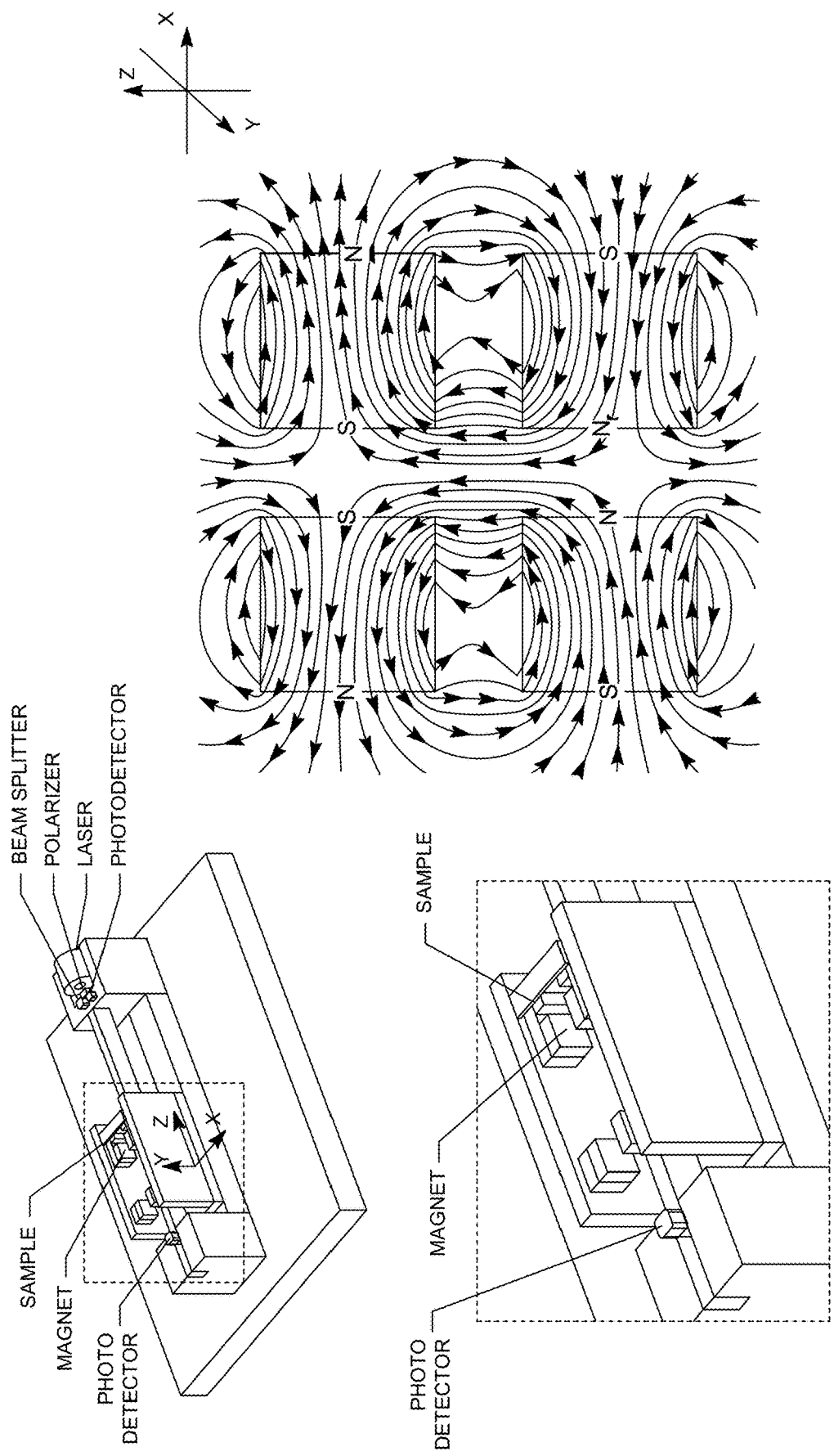
FIG. 9 is an illustration of an example of the magnetic field that can be delivered to detect or discern crystals in the biofluid sample.
Figure 10:
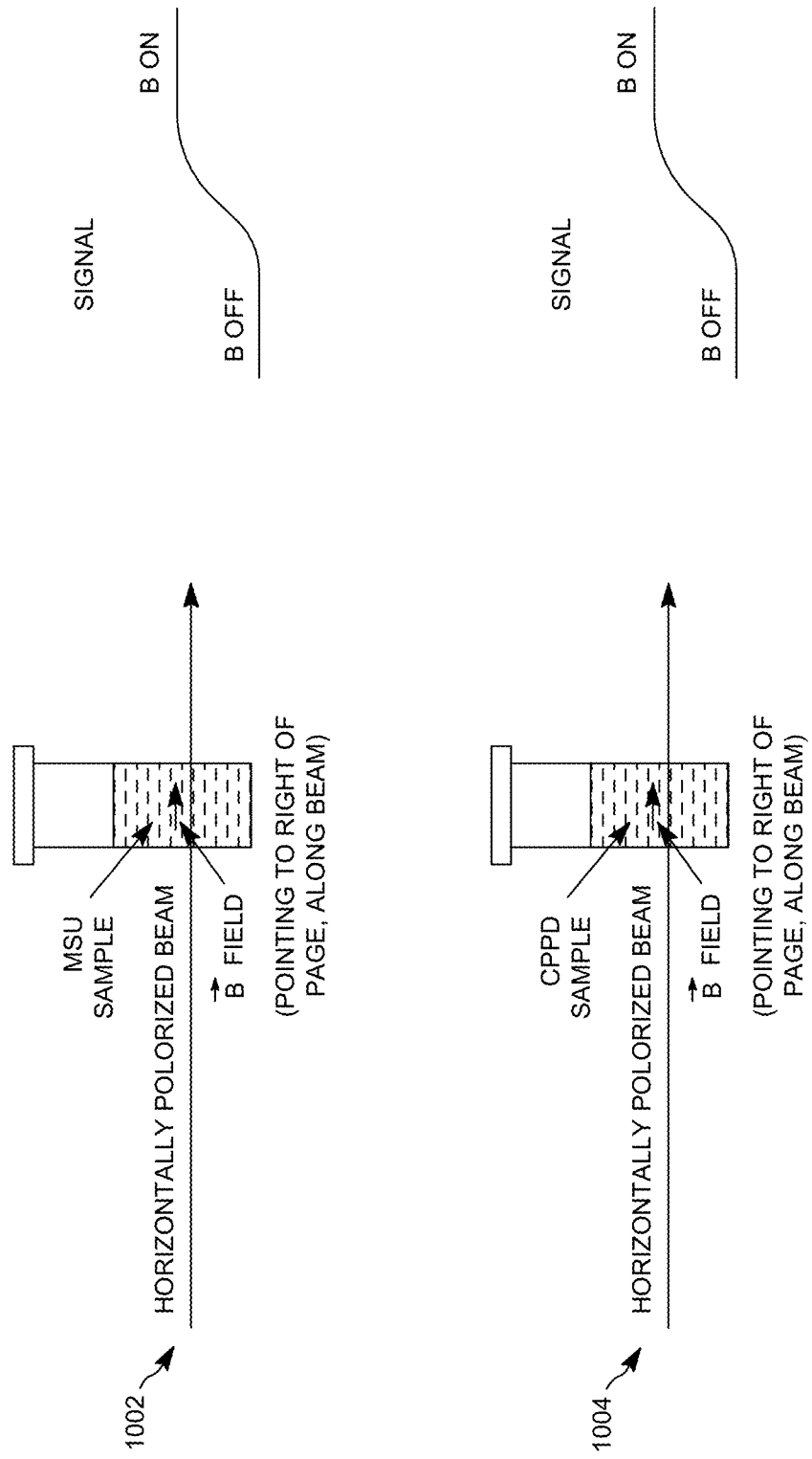
FIG. 10 is an illustration of example light signals under application of the magnetic field shown in FIGS. 6 and 9 used in detection or discernment of crystals in the biofluid sample.

Any different type of crystal within a biofluid can be identified and/or distinguished in this manner by examining magneto-optical properties under an appropriate one or more of the magnetic fields shown. For example, a "horizontal" direction "parallel" to the light beam (the magnetic field is established in a direction along the z-axis, while the light beam also travels along the z-axis). The configuration of this type of device is shown in FIG. 9. Although, as shown in FIG. 10, gout and pseudogout show the same type of resultant light intensity, with different crystals, the properties would change to be distinguishable under the vertical perpendicular magnetic field.

Another way to detect crystals in a biofluid sample and to discern the type of crystals can include changing the polarization direction of the light under the same magnetic field. The presence of crystals can be first detected in the biofluid sample by applying a magnetic field in a direction as light travels through the sample. The detected crystal can be one of two similar crystal types that may be in the biofluid sample. The two similar crystal types can exhibit different magneto-optical properties under a magnetic field, but with the polarization direction of the light being in a different direction. Accordingly, the type of crystal can be discerned by changing the polarization direction of the light and then again applying the magnetic field as light travels through the sample. Discernment of the type of crystal can lead to diagnosis of the particular disease condition and subsequent proper treatment of the disease condition.

Figure 11:
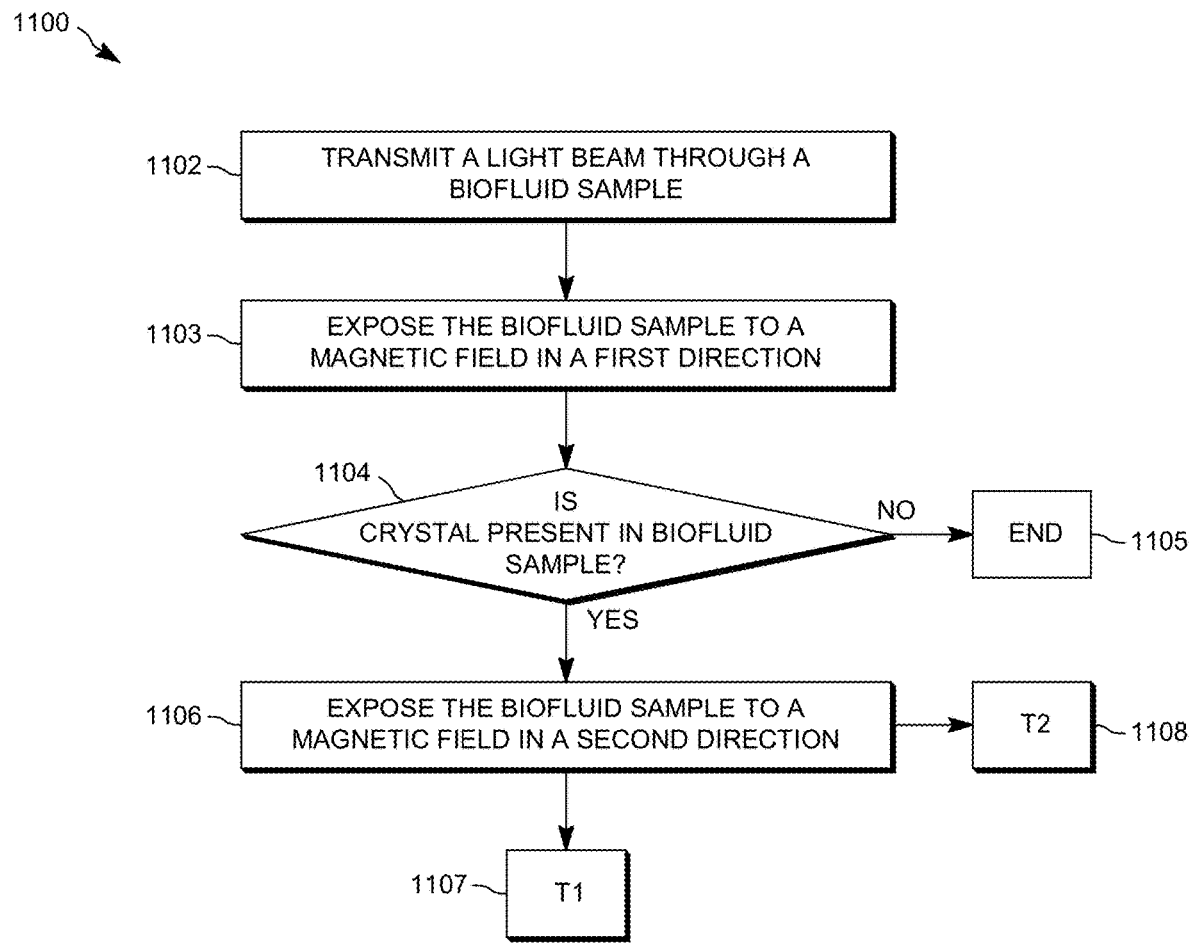
FIG. 11 is a process flow diagram of an example method for detecting and discerning crystals in a biofluid sample based on one or more magneto-optical properties.

In view of the foregoing structural and functional features described above, example methods will be better appreciated with reference to FIG. 11. While, for purposes of simplicity of explanation, the method of FIG. 11 is shown and described as executing serially, it is to be understood and appreciated that the present invention is not limited by the illustrated order, as some actions could, in other examples, occur in different orders from that shown and described herein or could occur concurrently. It will be appreciated that some or all acts of this method 1100 can be implemented as machine-readable instructions on a non-transitory computer readable medium.

FIG. 11 illustrates an example of a method 1100 for detecting and discerning crystals in a biofluid sample based on one or more magneto-optical properties. At element 1102, a light beam can be transmitted (by light source 12) through a biofluid sample (e.g. sample 16). The light beam can be polarized in a direction. The light beam can be transmitted from the light source to a light detector (e.g. detector 14). For example, the biofluid sample can be collected from a patient when the crystals are suspected of being within the biofluid.

At element 1103, the biofluid sample can be exposed to a magnetic field in a first direction (e.g. the sample can be between magnets 18 oriented to deliver the magnetic field in the first direction relative to the light). In some instances, the detection of crystals and discernment between the types of crystals can occur under the same magnetic field direction, but the direction of the light polarization can change.

At element 1104, a determination can be made whether the crystal is present in the biofluid sample (e.g. based on the intensity of the light passed through the sample under the magnetic field in the first direction). At element 1105, when no crystal is detected in the biofluid sample, the method can end. However, when crystal is detected in the biofluid sample, at element 1106 the biofluid sample can be exposed to a magnetic fluid in a second direction (e.g. the sample can move between magnets 18 oriented to deliver the magnetic field in the second direction relative to the light). Depending on the intensity of the light signal detected, the crystal can be classified as type 1 (T1) at element 1107 or type 2 (T2) at element 1108. For example, this classification can be accomplished by a device comprising a processor (e.g. a controller or other computing device). The determination can lead to a diagnosis—e.g. of gout or pseudogout—based on the light intensity passing through the crystals under the magnetic field in the second direction.

EXAMPLE

The following example is for the purpose of illustration only and is not intended to limit the scope of the appended claims. Crystals can be detected and discerned in a biofluid sample based on magneto-optical properties. As shown in this example, monosodium urate (MSU) crystals that cause gout and calcium pyrophosphate dihydrate (CPPD) crystals that cause pseudogout exhibit different magneto-optical properties. The different exhibited magneto-optical properties can be used to detect and discern the crystals.

Synthetic Crystal Preparation

Figure 12:
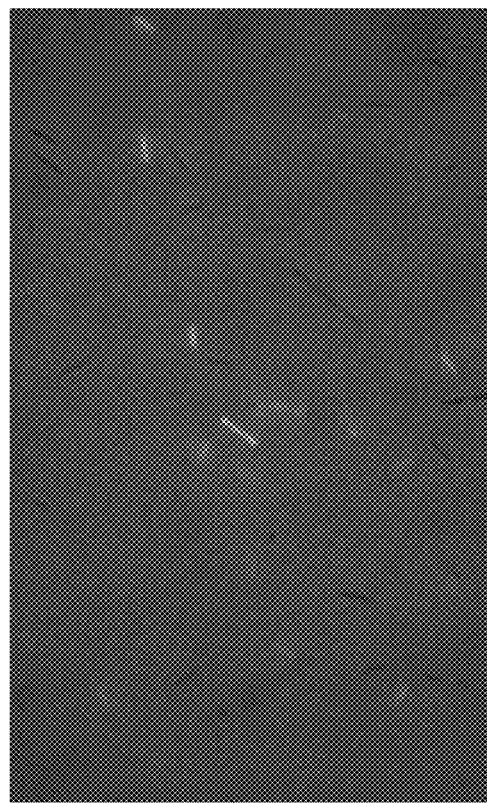
FIG. 12 shows microscopic images of synthetic MSU and CPPD crystals used in this study.
Figure 12:
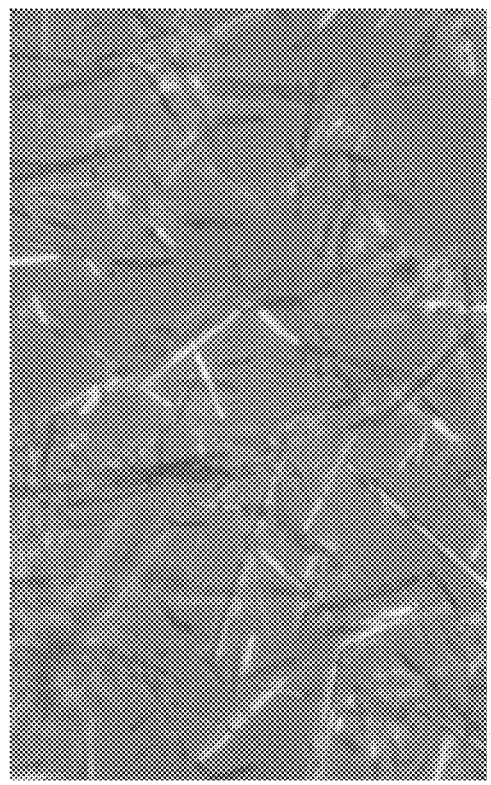

Synthetic samples of MSU and CPPD are prepared by suspending each in a phosphate buffered saline (PBS) solution. Images of the synthetic MSU and CPPD crystals used in this study are shown in FIG. 12. The dimensions and shapes of the synthetic crystals in PBS are comparable to those observed clinically in synovial fluid. The concentration of the crystals is kept between 10 and 100 µg/ml, which is the range of clinical concentrations generally found in the synovial fluid of patients suffering from gout or pseudogout.

The synthetic samples of MSU and CPPD mimic gout and pseudogout, respectively. Clinical samples could be collected as follows. Synovial fluid is collected by aspiration. The fluid is processed through standard digestion methods and then diluted with PBS solution.

Polarized Laser Source—No External Magnetic Field

A horizontally polarized laser source is directed through the synthetic samples of MSU and CPPD without the presence of an external magnetic field. In the absence of any magnetic field the crystals are randomly oriented in the PBS solution.

Polarized Laser Source—External Magnetic Field

Figure 13:
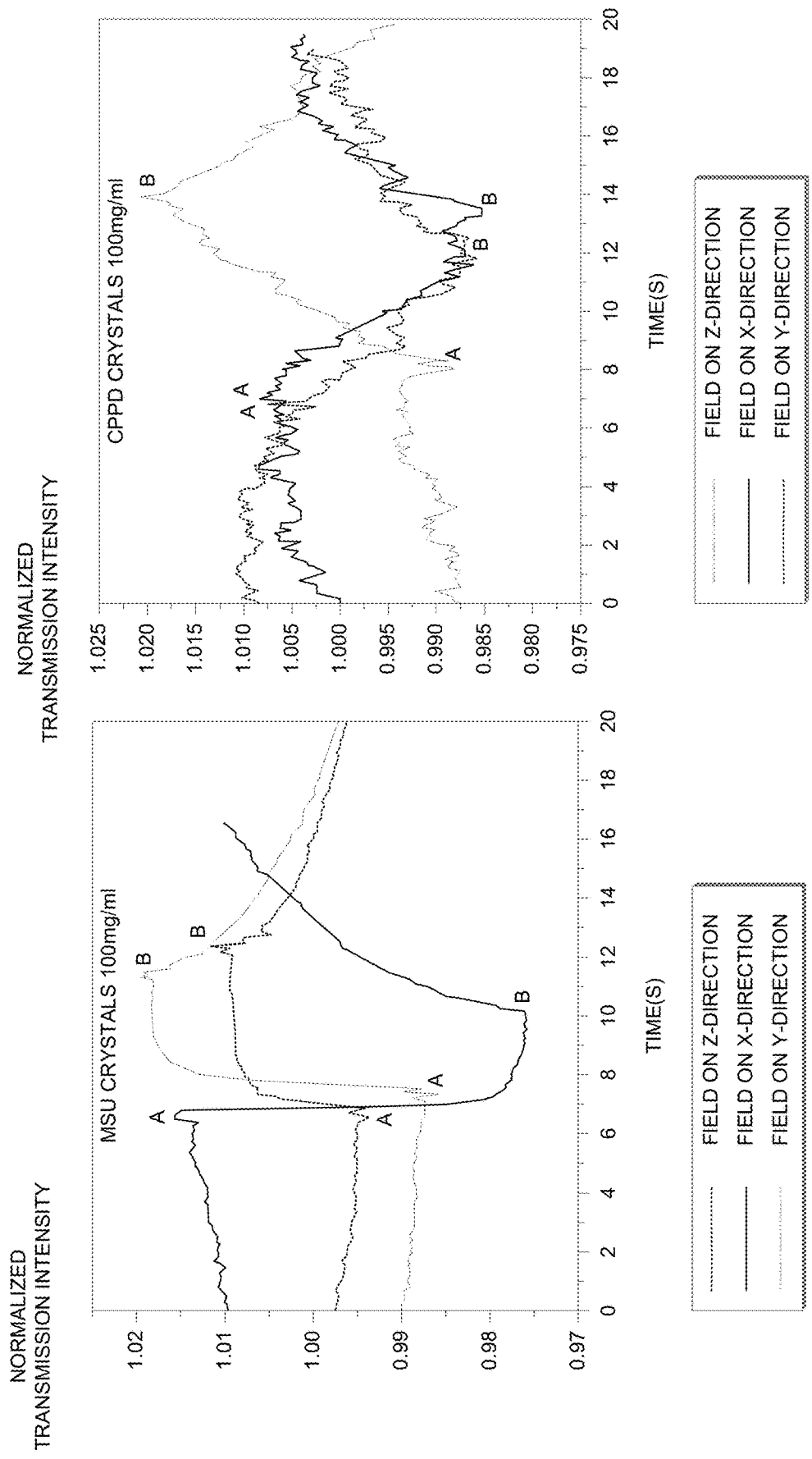
FIG. 13 shows normalized transmission signal intensity changes with a magnet inserted at A and removed at B.

The horizontally polarized laser source is directed through the synthetic samples of MSU and CPPD with the external magnetic field turned on (using Neodymium permanent magnets on either side of the sample). The external magnetic field is applied in one of three different directions: vertical (y-direction, FIG. 7), along the direction of the laser beam (z-direction, FIG. 9), and horizontal across the sample (x-direction, FIG. 4). In the presence of the external magnetic field, the crystals tend to align perpendicularly to the field. FIG. 13 shows the change in normalized transmission intensity for MSU and CPPD crystals at all three positions for a liquid sample with a concentration of 100 µg/ml.

Magneto-Optical Properties

The MSU crystal exhibits dichroic characteristics as the magnetic field direction changes from vertical to horizontal (perpendicular to the beam). More light is transmitted in the vertical position of the magnetic field compared to this horizontal position of the magnetic field. When the magnetic field is along the direction of the incident light beam, transmission intensity increases.

The CPPD crystal exhibits a decrease in transmission goes down in both the vertical position of the magnetic field and the horizontal position of the magnetic field. When the magnetic field is along the direction of the incident light beam, transmission intensity increases, with the CPPD showing more sensitivity for this direction.

Figure 14:
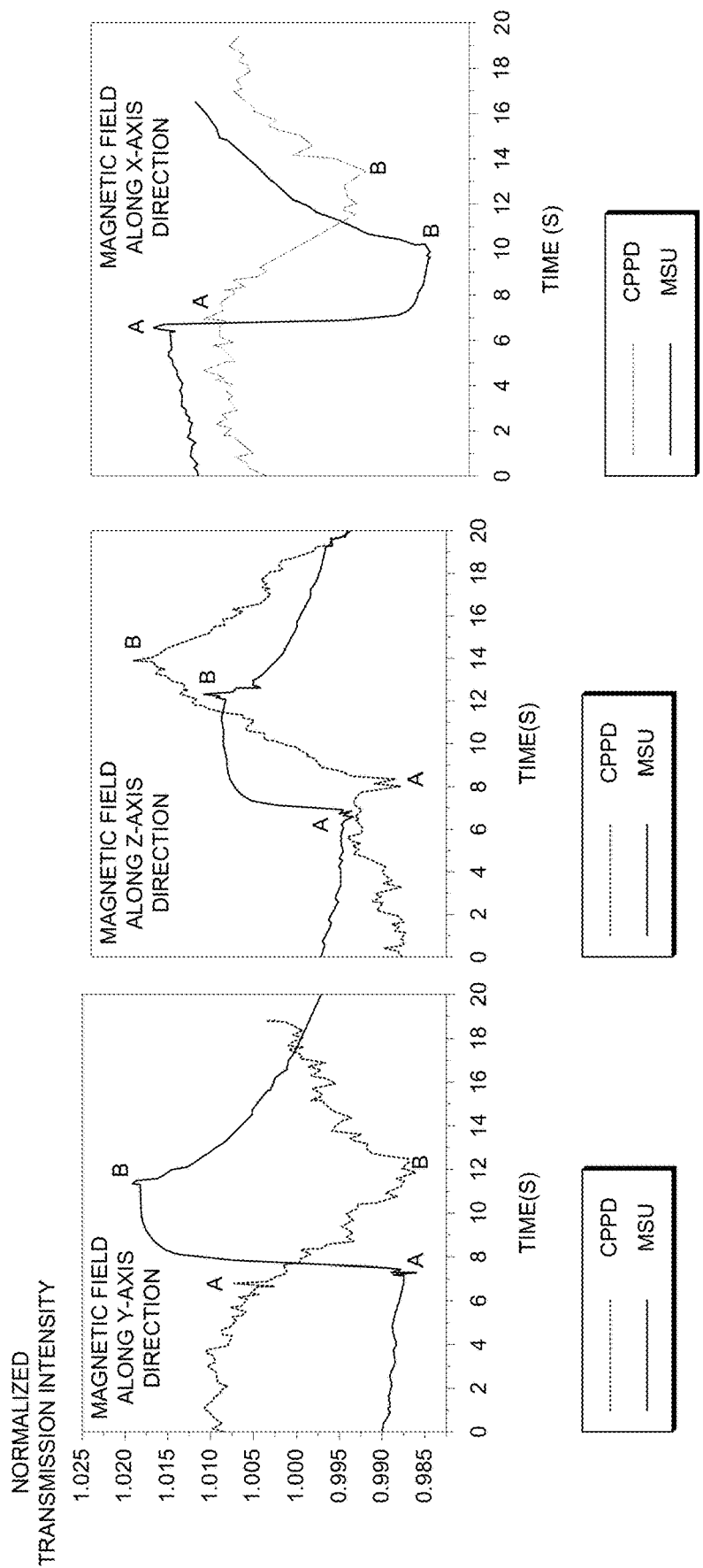
FIG. 14 shows the MSU and CPPD response at different field direction.

FIG. 14 shows a comparison of the MSU and CPPD crystal-sample responses at different orientations of the magnetic field.

Figure 15:
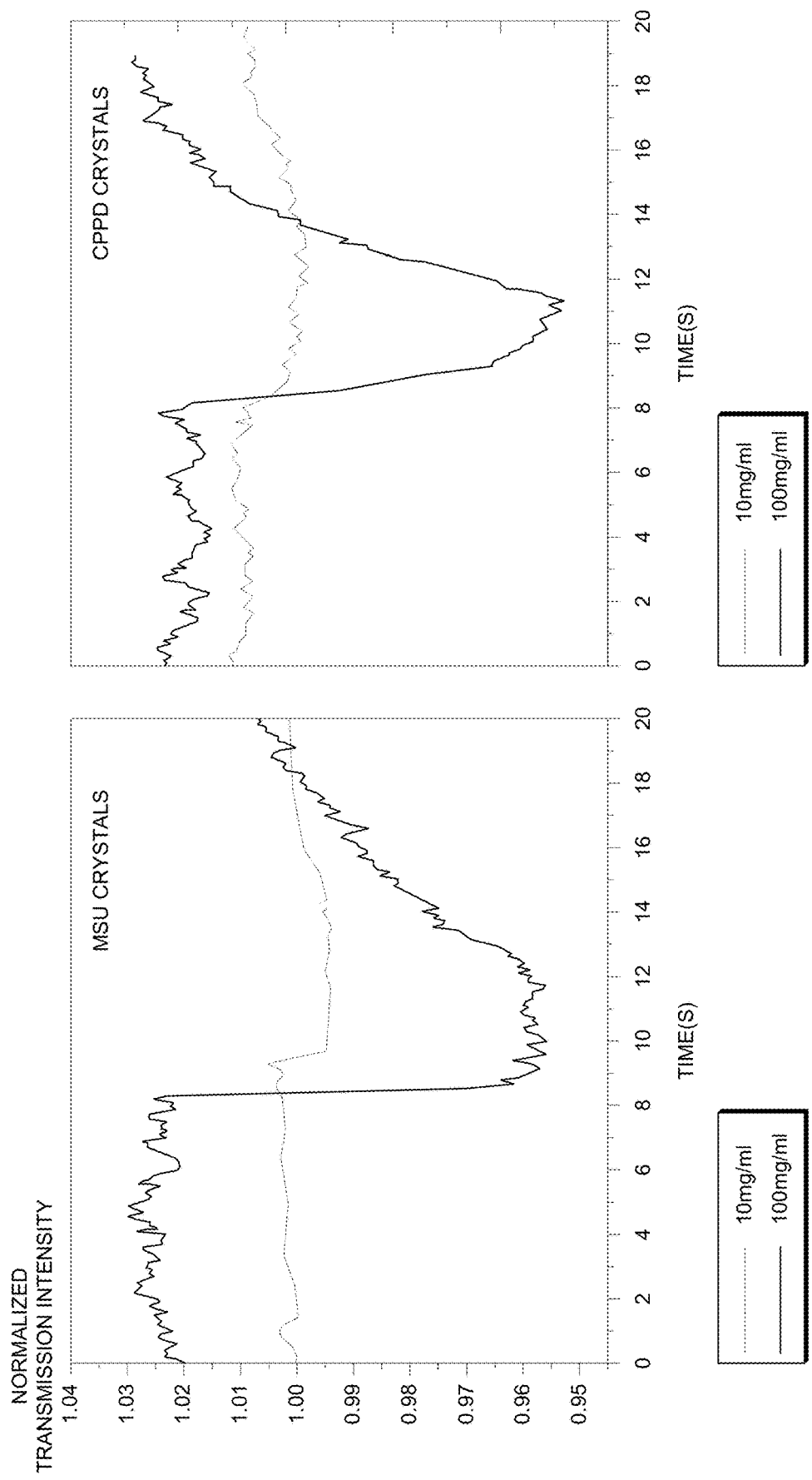
FIG. 15 shows how the amplitude changes with different concentrations of crystals.

When the field is removed, the relaxation time of the MSU and CPPD crystals depends on the size of the crystals. FIG. 15 shows the signal transmission intensity for two different concentrations of MSU and two different concentrations of CPPD. As shown in FIG. 15, for each of the two different concentrations, the MSU crystals take a longer time to relax due to their longer size (generally 5 to 40 microns), while CPPD crystals relax more quickly due to their smaller size (generally 1 to 10 microns). The change in transmission amplitude of the signal is dependent on the concentration of the crystals.

The aspects of this disclosure have been described illustratively. Accordingly, the terminology employed throughout the disclosure should be read in an exemplary rather than a limiting manner. Although minor modifications of the invention will occur to those well versed in the art, it shall be understood that what is intended to be circumscribed within the scope of the patent warranted hereon are all such embodiments that reasonably fall within the scope of the advancement to the art hereby contributed, and that that scope shall not be restricted.

References to "one embodiment", "an embodiment", "some embodiments", "one example", "an example", "some examples" and so on, indicate that the embodiment(s) or example(s) so described may include a particular feature, structure, characteristic, properly, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

Where the disclosure or claims recite "a," "an," "a first," or "another" element, or the equivalent thereof, it should be interpreted to include one or more than one such element, neither requiring nor excluding two or more such elements. Furthermore, what have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims.

What is claimed is:

1. A system comprising:
   one or more controllers;
   a diagnostic device comprising:
   a sample holder, moveable between a first position and a second position and holding a biofluid sample;
   a light source that transmits a light beam in a direction towards a light detector through the first position and then the second position of the sample holder, wherein the sample holder moves parallel to the direction of the transmission of the light beam;
   a detection area at the first position, the detection area defined by a first plurality of magnets in a first configuration with at least two magnets on opposite sides of the sample holder to generate a first magnetic field that transects the light beam in a first direction to alter the light beam in a first manner when the biofluid sample within the sample holder is in the first position;
   a discernment area at the second position, the discernment area defined by a second plurality of magnets, separate and distinct from the first plurality of magnets, in a second configuration with at least two magnets on opposite sides of the sample holder to generate a second magnetic field that transects the light beam in a second direction, different from the first direction, to alter the light beam in a second manner, different from the first manner, when the biofluid sample within the sample holder is in the second position; and
   the light detector on the opposite side of the light source that receives the light beam altered in the first manner under the first magnetic field when the sample holder is in the first position and altered in the second manner under the second magnetic field when the sample holder is in the second position, the one or more controllers operate the diagnostic device in at least a partially automated fashion, the one or more controllers are programmed to execute instructions to:

with the sample holder in the first position, expose the biofluid sample in the sample holder to the first magnetic field that transects the light beam in the first direction to alter the light beam in the first manner, collect, via the light detector, the light beam altered in the first manner under the first magnetic field and determine whether a crystal is present in the biofluid sample based on an intensity of the light beam received when altered in the first manner, and if the crystal is determined to be present in the biofluid sample, then move the sample holder to the second position, expose the biofluid sample in the sample holder to the second magnetic field that transects the light beam in the second direction to alter the light beam in the second manner, collect, via the light detector, the light beam altered in the second manner under the second magnetic field and discern a type of the crystal that is present in the biofluid sample based on an intensity of the light beam received when altered in the second manner.

2. The system of claim 1, wherein the first plurality of magnets and the second plurality of magnets each comprises at least one permanent magnet.

3. The system of claim 1, wherein the first plurality of magnets and/or the second plurality of magnets comprises at least four magnets.

4. The system of claim 3, wherein each of the at least four magnets is a permanent magnet.

5. The system of claim 1, wherein the controller can discern the type of the crystal is one of a monosodium urate (MSU) crystal and a calcium pyrophosphate dihydrate (CPPD) crystal.

6. The system of claim 5, wherein the magnetic field in the second direction is vertical to the light beam and the controller discerns the type of crystal in the biofluid sample is MSU crystal when the intensity of the light beam received when altered in the second manner is increased.

7. The system of claim 5, wherein the magnetic field in the second direction is vertical to the light beam and the controller discerns the type of crystal in the biofluid sample is CPPD crystal when the intensity of the light beam received when altered in the second manner is decreased.

8. A system comprising:
a diagnostic device comprising:
a sample holder, moveable between a first position in a detection area and a second position in a discernment area and holding a synovial fluid sample, wherein the detection area is separate from the discernment area;
a light source that transmits a light beam in a direction towards a light detector through the first position and then the second position of the sample holder, wherein the sample holder moves parallel to the direction of the transmission of the light beam;
the detection area defined by a first plurality of magnets configured with at least two magnets on opposite sides of the sample holder to generate a first magnetic field that transects the light beam in a horizontal direction to alter the light beam in a first manner when the sample holder is in the first position and the synovial fluid sample within the sample holder is transected by the light beam;
the discernment area defined by a second plurality of magnets, separate and distinct from the first plurality of magnets, configured with at least two magnets on opposite sides of the sample holder to generate a second magnetic field that transects the light beam in a vertical direction to alter the light beam in a second manner when the sample holder is in the second position and the synovial fluid sample within the sample holder is transected by the light beam; and
the light detector that receives the light beam altered in the first manner under the first magnetic field when the sample holder is in the first position and altered in the second manner under the second magnetic field when the sample holder is in the second position;

a controller configured to operate the diagnostic device in at least a partially automated fashion, the controller programmed to execute instructions to:
move the sample holder to the first position in the detection area to detect if a crystal is present in the synovial fluid sample; and
if the crystal is detected to be present, move the sample holder to the second position in the discernment area to discern if the crystal present in the synovial fluid sample is a monosodium urate (MSU) crystal or a calcium pyrophosphate dihydrate (CPPD) crystal, and a sampling device configured to control the light detector and to determine if at least one of MSU crystal or CPPD crystal is present in a synovial fluid sample, the sampling device comprising a controller programmed to execute instructions to:
collect, via the light detector, the light beam altered in the first manner under the first magnetic field in the horizontal direction when the sample holder is in the first position in the detection area and the light beam transects the synovial fluid sample, and
determine whether the crystal is present in the synovial fluid sample based on an intensity of the light beam received when altered in the first manner, and
if the crystal is determined to be present in the biofluid sample, then with the sample holder moved to the second position:
collect, via the light detector, the light beam altered in the second manner under the second magnetic field in the horizontal direction when the sample holder is in the second position in the discernment area and the light beam transects the synovial fluid sample, and
discern if the intensity of the light beam received when altered in the second manner is more or less intense than when altered in the first manner, wherein:
if the intensity of the light beam is more intense then the crystal present in the synovial fluid sample is MSU crystal, and
if the intensity of the light beam is less intense then the crystal present in the synovial fluid sample is CPPD crystal.

* * * * *